`US012159717B2`

United States Patent
Kerman et al.

(10) Patent No.: US 12,159,717 B2
(45) Date of Patent: Dec. 3, 2024

(54) RESPIRATORY RATE PREDICTION FROM A PHOTOPLETHYSMOGRAM

(71) Applicant: Owlet Baby Care, Inc., Lehi, UT (US)

(72) Inventors: Sean Kerman, Lehi, UT (US); Tanner Christensen, Provo, UT (US); Chris Hettinger, Worcester, MA (US); Jeffrey Humpherys, Lehi, UT (US)

(73) Assignee: OWLET BABY CARE, INC., Lehi, UT (US)

( * ) Notice: Subject to any disclaimer, the term of this patent is extended or adjusted under 35 U.S.C. 154(b) by 946 days.

(21) Appl. No.: 17/065,453

(22) Filed: Oct. 7, 2020

(65) Prior Publication Data

US 2021/0110927 A1  Apr. 15, 2021

Related U.S. Application Data

(60) Provisional application No. 62/939,816, filed on Nov. 25, 2019, provisional application No. 62/911,879, filed on Oct. 7, 2019.

(51) Int. Cl.
*G16H 50/20*  (2018.01)
*A61B 5/00*  (2006.01)
(Continued)

(52) U.S. Cl.
CPC .......... *G16H 50/20* (2018.01); *A61B 5/0806* (2013.01); *A61B 5/7257* (2013.01);
(Continued)

(58) Field of Classification Search
CPC ...... G16H 50/20; G16H 50/30; A61B 5/0806; A61B 5/7257; A61B 5/7264; A61B 5/7267; A61B 5/7275; G06N 3/04; G06N 3/08
See application file for complete search history.

(56) References Cited

U.S. PATENT DOCUMENTS 3,045,678 A    7/1962  Geimer
3,080,869 A    3/1963  Alberts
(Continued)

FOREIGN PATENT DOCUMENTS

CN    107979554 B    10/2019
CN    112203582 A    1/2021
(Continued)

OTHER PUBLICATIONS

US 2022/0192529 A1, 06/2022, Al-Ali et al. (withdrawn)
(Continued)

*Primary Examiner* — Alexey Shmatov
*Assistant Examiner* — Beatriz Ramirez Bravo
(74) *Attorney, Agent, or Firm* — Workman Nydegger

(57) ABSTRACT

A technology for obtaining a respiratory rate from a photoplethysmogram (PPG) signal. In one example, an artificial neural network model can be trained to predict a respiratory rate using a training dataset containing PPG data. The artificial neural network model can include a first series of convolutional layers to remove artifacts from a PPG signal, a fast Fourier transform (FFT) layer to convert the PPG signal to PPG frequency representations, and a dense layer to decode the PPG frequency representations to respiratory rate predictions. After training the artificial neural network model, PPG data generated by a pulse oximeter monitor can be obtained, and the PPG data can be input to the artificial neural network model. The artificial neural network model outputs a respiratory rate prediction, wherein the respiratory rate prediction represents the respiratory rate obtained from the PPG signal.

20 Claims, 18 Drawing Sheets

(51) Int. Cl.
  *A61B 5/08* (2006.01)
  *G06N 3/04* (2023.01)
  *G06N 3/08* (2023.01)
  *G16H 50/30* (2018.01)
  *A61B 5/024* (2006.01)
  *A61B 5/1455* (2006.01)

(52) U.S. Cl.
  CPC .......... *A61B 5/7264* (2013.01); *A61B 5/7267* (2013.01); *A61B 5/7275* (2013.01); *G06N 3/04* (2013.01); *G06N 3/08* (2013.01); *G16H 50/30* (2018.01); *A61B 5/02416* (2013.01); *A61B 5/14551* (2013.01)

(56) References Cited

U.S. PATENT DOCUMENTS

| | | |
|---|---|---|
| 5,255,393 A | 10/1993 | Brady |
| 5,571,039 A | 11/1996 | Ford |
| 5,609,156 A | 3/1997 | Keith et al. |
| 5,666,959 A | 9/1997 | Deans et al. |
| 5,853,364 A | 12/1998 | Baker et al. |
| 6,093,151 A | 7/2000 | Shine et al. |
| 6,340,346 B1 | 1/2002 | Almog et al. |
| 7,333,850 B2 | 2/2008 | Marossero et al. |
| 7,937,128 B2 | 5/2011 | Al-Ali |
| 7,937,130 B2 | 5/2011 | Diab et al. |
| 7,949,389 B2 | 5/2011 | Wolfberg et al. |
| 8,116,855 B2 | 2/2012 | James et al. |
| 8,265,723 B1 | 9/2012 | McHale et al. |
| 8,275,451 B2 | 9/2012 | Marossero et al. |
| 8,747,186 B2 | 6/2014 | Fong |
| 8,764,686 B2 | 7/2014 | Nishihara et al. |
| 8,847,740 B2 | 9/2014 | Kiani et al. |
| 8,892,181 B2 | 11/2014 | Wolfberg et al. |
| 8,965,471 B2 | 2/2015 | Lamego |
| 9,060,722 B2 * | 6/2015 | Teixeira ................. A61B 5/318 |
| 9,173,613 B2 | 11/2015 | Igney et al. |
| 9,392,952 B1 | 7/2016 | Oz et al. |
| 9,456,637 B2 | 10/2016 | Fligel |
| 9,591,983 B2 | 3/2017 | Amir et al. |
| 9,597,001 B2 | 3/2017 | Zigel et al. |
| 9,693,719 B2 | 7/2017 | Al-Ali et al. |
| 9,693,730 B2 | 7/2017 | Workman et al. |
| 9,717,412 B2 | 8/2017 | Roham et al. |
| 9,730,476 B1 | 8/2017 | Mahar |
| 9,730,640 B2 | 8/2017 | Diab et al. |
| 9,867,575 B2 | 1/2018 | Maani et al. |
| 9,936,917 B2 | 4/2018 | Poeze et al. |
| 9,968,291 B2 | 5/2018 | Hayes-Gill et al. |
| 10,080,389 B2 | 9/2018 | Melarti et al. |
| 10,085,697 B1 | 10/2018 | Evans |
| 10,149,616 B2 | 12/2018 | Al-Ali et al. |
| 10,265,010 B2 | 4/2019 | Larson |
| 10,278,604 B2 | 5/2019 | Kimura et al. |
| 10,456,074 B2 | 10/2019 | Penders et al. |
| 10,482,962 B2 | 11/2019 | Kim et al. |
| 10,575,779 B2 | 3/2020 | Poeze et al. |
| 10,709,335 B2 | 7/2020 | Matsuoka et al. |
| 10,721,785 B2 | 7/2020 | Al-Ali |
| 10,736,507 B2 | 8/2020 | Muhsin et al. |
| 10,918,341 B2 | 2/2021 | Al-Ali et al. |
| 10,987,484 B1 | 4/2021 | Konda et al. |
| 11,003,987 B2 * | 5/2021 | Roblek .................... G06N 3/08 |
| 11,446,466 B1 | 9/2022 | Shvartzman et al. |
| 11,504,002 B2 | 11/2022 | Muhsin et al. |
| 11,504,062 B2 | 11/2022 | Poeze et al. |
| 2001/0014776 A1 | 8/2001 | Oriol et al. |
| 2004/0145089 A1 | 7/2004 | Burrows |
| 2005/0267377 A1 | 12/2005 | Marossero et al. |
| 2009/0069647 A1 * | 3/2009 | McNames .............. A61B 5/412 600/301 |
| 2010/0113893 A1 | 5/2010 | Cohen et al. |
| 2012/0016209 A1 | 1/2012 | Wolfberg et al. |
| 2014/0275832 A1 | 9/2014 | Meuhlsteff |
| 2014/0307423 A1 | 10/2014 | Coats |
| 2015/0150538 A1 | 6/2015 | Reuter et al. |
| 2015/0374328 A1 | 12/2015 | Ginestet et al. |
| 2016/0076175 A1 | 3/2016 | Rock et al. |
| 2016/0097716 A1 | 4/2016 | Gulati et al. |
| 2016/0198969 A1 | 7/2016 | Cheng et al. |
| 2016/0220188 A1 | 8/2016 | Chon et al. |
| 2016/0262649 A1 | 9/2016 | Hayes-Gill et al. |
| 2017/0036066 A1 | 2/2017 | Chahine |
| 2017/0095212 A1 | 4/2017 | Albadawi et al. |
| 2017/0156593 A1 | 6/2017 | Ferber et al. |
| 2017/0224268 A1 | 8/2017 | Altini et al. |
| 2017/0265799 A1 | 9/2017 | Du et al. |
| 2018/0007977 A1 | 1/2018 | Windenberger |
| 2018/0110434 A1 | 4/2018 | Lau et al. |
| 2018/0317878 A1 | 11/2018 | Wohlschlager et al. |
| 2018/0344171 A1 | 12/2018 | Straka et al. |
| 2018/0345015 A1 | 12/2018 | Straka et al. |
| 2018/0360315 A1 * | 12/2018 | Fujita ....................... A61B 5/02 |
| 2019/0000384 A1 | 1/2019 | Gupta et al. |
| 2019/0104951 A1 | 4/2019 | Valys et al. |
| 2019/0133468 A1 | 5/2019 | Aliamiri et al. |
| 2019/0142288 A1 * | 5/2019 | Aliamiri .............. A61B 5/6885 600/301 |
| 2019/0286233 A1 | 9/2019 | Newberry |
| 2019/0313929 A1 | 10/2019 | Sana et al. |
| 2019/0320875 A1 | 10/2019 | Jones et al. |
| 2019/0344042 A1 | 11/2019 | Garcia Molina et al. |
| 2020/0003858 A1 | 1/2020 | Takeshima |
| 2020/0054289 A1 | 2/2020 | Shimol et al. |
| 2020/0066296 A1 | 2/2020 | Sargsyan et al. |
| 2020/0113470 A1 | 4/2020 | Friedman et al. |
| 2020/0146623 A1 | 5/2020 | Anushiravani et al. |
| 2020/0253474 A1 | 8/2020 | Muhsin et al. |
| 2020/0375512 A1 * | 12/2020 | Lu ....................... A61B 5/0022 |
| 2021/0161442 A1 | 6/2021 | Welch et al. |
| 2021/0353156 A1 | 11/2021 | Rong et al. |
| 2022/0218291 A1 | 7/2022 | Al-Ali et al. |
| 2022/0248984 A1 | 8/2022 | Poeze et al. |
| 2023/0157543 A1 | 5/2023 | Muhsin et al. |
| 2023/0165530 A1 | 6/2023 | Poeze et al. |
| 2023/0284943 A1 | 9/2023 | Scruggs et al. |
| 2023/0301562 A1 | 9/2023 | Scruggs et al. |

FOREIGN PATENT DOCUMENTS

| | | | |
|---|---|---|---|
| CN | 109199375 B | 11/2021 | |
| GB | 2563112 A | 12/2018 | |
| JP | H10-506034 A | 6/1998 | |
| KR | 960010976 B1 | 8/1996 | |
| WO | WO 96/08996 A2 | 3/1996 | |
| WO | WO 2014/192002 A1 | 12/2014 | |
| WO | WO-2016110804 A1 * | 7/2016 | ............... A61B 3/16 |
| WO | WO 2017/063086 A1 | 4/2017 | |
| WO | WO 2017/171637 A1 | 5/2017 | |
| WO | WO-2017079052 A1 * | 5/2017 | ........... G06K 9/6268 |
| WO | WO 2017/096358 | 6/2017 | |
| WO | WO 2018/160446 | 9/2018 | |
| WO | WO 2018/160446 A8 | 9/2018 | |
| WO | WO 2018/160890 A1 | 9/2018 | |
| WO | WO 2018/161152 A1 | 9/2018 | |
| WO | WO 2018/211403 A1 | 11/2018 | |
| WO | WO 2019/006536 A1 | 1/2019 | |
| WO | WO 2019/048775 | 3/2019 | |
| WO | WO 2019/134031 A2 | 7/2019 | |
| WO | WO 2019/134032 A9 | 7/2019 | |
| WO | WO 2019/134033 A2 | 7/2019 | |
| WO | WO 2019/140704 A1 | 7/2019 | |
| WO | WO 2019/190185 A1 | 10/2019 | |
| WO | WO 2019/190208 A1 | 10/2019 | |
| WO | WO 2020/072297 | 4/2020 | |

OTHER PUBLICATIONS

Roy et al., Improving Photoplethysmographic Measurements Under Motion Artifacts Using Artificial Neural Network for Personal Healthcare, IEEE (Dec. 2018) (Year: 2018).*

(56) References Cited

OTHER PUBLICATIONS

Perna, "Convolutional Neural Networks Learning from Respiratory Data", IEEE (2018) (Year: 2018).*

Irusta et al., Cerebral Oximetry versus Photoplethysmography to Monitor Respiratory Rate, Computing in Cardiology (2016) (Year: 2016).*

Birrenkott et al., Robust Estimation of Respiratory Rate via ECG and PPG-Derived Respiratory Quality Indices, IEEE (2016) (Year: 2016).*

Johansson, Neural Network for photoplethysmographic respiratory rate monitoring, Bio-Optics in Medicine (2002) (Year: 2002).*

D. Biswas et al., "CorNET: Deep Learning Framework for PPG-Based Heart Rate Estimation and Biometric Identification in Ambulant Environment," in IEEE Transactions on Biomedical Circuits and Systems, vol. 13, No. 2, pp. 282-291, Apr. 2019, doi: 10.1109/TBCAS.2019.2892297. (Year: 2019).

H. Chung et al. "Feasibility Study of Deep Neural Network for Heart Rate Estimation from Wearable Photoplethysmography and Acceleration Signals," 2019 International Conference of the IEEE Engineering in Medicine and Biology Society (EMBC), 2019, pp. 3633-3636, doi: 10,11 (Year: 2019).

Bagha et al. (2011). A Real Time Analysis of PPG Signal of Measurement of Sp02 and Pulse Rate. International Journal of Computer Applications. (Year: 2011).

Iowa head and Neck Protocols. Pulse Oximetry Basic Principles and Interpretation; Iowa Head and Neck Protocols. (n.d.). Retrieved Aug. 29, 2022, from https://medicine.uiowa.edu/iowaprotocols/pulse-oximetry-basic-principles-and-interpretation (Year: 2017).

Yeh et al. Using a Calculated Pulse Rate with an Artificial Neural Network to Detect Irregular Interbeats. J Med Syst 40, 48 (2016). https://doi.org//10.1007.s10916-015-0409-x (Year: 2016).

Markos et al., Automatic arrythmia detection based on time and time-frequency analysis of heart rate variability, Computer Methods and Programs in Biomedicine, vol. 74, Issue 2, (Year: 2004).

T. Schäck et al. "Computationally efficient heart rate estimation during physical exercise using photoplethysmographic signals," 2017 25$^{th}$ European Signal Processing Conference (EUSIPCO), 2017, pp. 2478-2481, doi: 10.23919/EUSIPCO.2017.8081656. (Year: 2017).

A. Rueda et al. "Augmenting Dysphonia Voice Using Fourier-based Synchrosqueezing Transform for a CNN Classifier," ICASSP 2019-2019 IEEE International Conference on Acoustics, Speech and Signal Processing (ICASSP), 2019, pp. 6415-6419, doi: 10.1109/ICASSP.2019.8682391. (Year: 2019).

Hassan et al.. (2017). Diagnosis of Focal Liver Diseases Based on Deep Learning Technique for Ultrasound Images. Arabian Journal for Science and Engineering. 42. 10.1007/s13369-016-2387-9. (Year: 2017).

Ge et al. Cardiac arrythmia classification using autoregressive modeling. BioMed Eng OnLine 1 , (2002). https://org/10.1186/1475.925X-1-5 (Year: 2002).

F. Xiao et al. Heart Rate Prediction Model Based on Physical Activities Using Evolutionary Computing, 2010, pp. 198-201, doi: 10.1109/ICGEC.2010.56. (Year 2010).

Tadic et al. Heart rate as a predictor of cardiovascular risk. Eur J Clin Invest. Mar. 2018;48(3). Doi: 10.111/eci.12892. Epub Feb. 5, 2018. PMID: 29355923. (Year: 2018).

M. Asaduzzaman et al. "Continuous heart rate and body temperature monitoring system using Arduino UNO and Android device," 2015 Electrical Information and Communication Technologies (EICT), 2015, pp. 183-191 (Year: 2015).

Amin et al.; "Separation of Fetal Electrocardiogram Composite ECG Using Adaptive Linear Neural Network for Fetal Monitoring;" International Journal of the Physical Sciences; (Oct. 2011); pp. 5871-5876; vol. 6, No. 24.

Azmed; "Maternity Belt—Belly Band for Pregnant Women to Support Back/Waist/Abdomen with Belly Brace—Breathable & Adjustable for Different Stages;" Amazon.com; (Aug. 22, 2015); 6 pages; [Retrieved on Dec. 12, 2021]; retrieved from <URL: https://www.amazon.com/AZMED-Maternity-Breathable-Abdominal-Support/dp/B0113WE0QS>.

Bailey; "Intrapartum Fetal Monitoring;" American Family Physicians; (Dec. 15, 2009); pp. 1388-1396; vol. 80, No. 12.

BLANQI®; "Blanqi® Everyday™ Maternity Built-In Support Bellyband;" (Oct. 3, 2019); 2 pages; [Retrieved on Dec. 12, 2021]; retrieved from <URL: https://www.blanqi.com/products/blanqi-maternity-support-bellyyband?variant=1114741357 >.

Hasan et al.; "Detection and Processing Techniques of FECG Signal for Fetal Monitoring;" Biological Procedures Online; (2009); pp. 263-295; vol. 11, No. 1; <doi: 10.1007/s12575-009-9006-z >.

Kaleem et al.; "An Efficient Approach for Fetal ECG Extraction;" International Journal of Computer Applications; (Dec. 2018); 5 pages; vol. 182, No. 33.

Noguchi et al.; "Neural Network Analysis and Evaluation of the Fetal Heart Rate;" Algorithms (2009); pp. 19-30; vol. 2, Issue 1; <doi: 10.3390/a2010019 >.

Yeh et al.; "A New Method to Derive Fetal Heart Rate from Maternal Abdominal Electrocardiogram: Monitoring Fetal Heart Rate during Cesarean Section;" PLoS One; (Feb. 13, 2015); 12 pages; vol. 10, No. 2; <doi: 10.1371/journal.pone.0117509 >.

Zhu et al.; "Heart Rate Monitoring during Physical Exercise from Photoplethysmography using Neural Network;" IEEE Sensors Letters; (2017); pp. 1-4; vol. 2, No. 3; <doi: 10.1109/LSEN.2018.2878207 >.

Shamsir et al., "Smart infant-monitoring system with machine learning model to detect physiological activities and ambient conditions," IEEE International Instrumentation and Measurement Technology Conference (I2MTC). IEEE, 2020, pp. 6.

* cited by examiner

RESPIRATORY RATE PREDICTION FROM A PHOTOPLETHYSMOGRAM

PRIORITY CLAIM

This application claims priority to Application Ser. No. 62/911,879 filed on Oct. 7, 2019 entitled RESPIRATORY RATE ESTIMATION FROM PHOTOPLETHYSMOGRAM and Application Ser. No. 62/939,816 filed on Nov. 25, 2019 entitled RESPIRATORY RATE PREDICTION FROM A PHOTOPLETHYSMOGRAM. Both of the foregoing applications are incorporated herein by reference in their entireties.

BACKGROUND

Non-invasive health monitoring devices are increasingly helping people to better monitor their health status both at an activity/fitness level for self-health tracking and at a medical level providing more data to clinicians with a potential for earlier diagnostic and guidance of treatment. Some consumer wearable devices have incorporated sensors for gathering biometric data, such as a pulse oximeter, which can be used to generate a photoplethysmogram (PPG). A PPG is an optically obtained plethysmogram which can be used to detect blood volume changes in the microvascular bed of living tissue.

A PPG can be obtained using a pulse oximeter which illuminates the skin and measures changes in light absorption. A pulse oximeter monitors the perfusion of blood to the dermis and subcutaneous tissue of the skin. With each cardiac cycle the heart pumps blood to the periphery causing a pressure pulse that distends the arteries and arterioles in the subcutaneous tissue. A change in volume caused by the pressure pulse is detected by illuminating the skin with the light from a light-emitting diode (LED) and then measuring the amount of light either transmitted or reflected to a photodiode. Also, a respiratory rate can be derived from a PPG signal using a baseline wander (BW), an amplitude modulation of the PPG (AM), and/or a frequency modulation of the respiratory rate (FM). To compute the respiratory rate, one or more of these signals can be extracted from the PPG signal and either a fast Fourier transform (FFT) or a peak detection algorithm can be used to identify the respiratory rate.

DETAILED DESCRIPTION

Technologies are described for extracting a respiratory rate from a photoplethysmogram (PPG) using a machine learning model. In one example, an artificial neural network model can be trained to predict a respiratory rate using a training dataset containing PPG data. The artificial neural network model can include a series of convolutional layers used to identify a PPG signal in the PPG data and remove artifacts contained in the PPG data, a fast Fourier transform (FFT) layer used to identify PPG frequencies in the PPG data, and a dense layer (also referred to as a dense decoding layer) used to decode a respiratory rate value from the PPG frequencies. After training the artificial neural network model, a PPG signal can be obtained from a pulse oximeter and PPG data representing the PPG signal can be input to the artificial neural network model, and the artificial neural network model outputs a respiratory rate prediction that represents a respiratory rate extracted from the PPG signal.

The network architecture of the artificial neural network model described herein provides improvements in the accuracy of respiratory rate predictions obtained from a PPG signal over previous methods for computing a respiratory rate from a PPG signal. In particular, the accuracy of respiratory rate predictions output by the artificial neural network model is improved by placing an FFT layer after a series of convolutional layers and providing the output of the FFT layer to a dense layer of the artificial neural network model. Placement of the FFT layer in this way improves the accuracy of respiratory rate predictions by using the FFT layer to identify fundamental and harmonic frequencies of a PPG signal, thereby reducing a number of parameters provided to the dense layer of the artificial neural network model.

Figure 1:
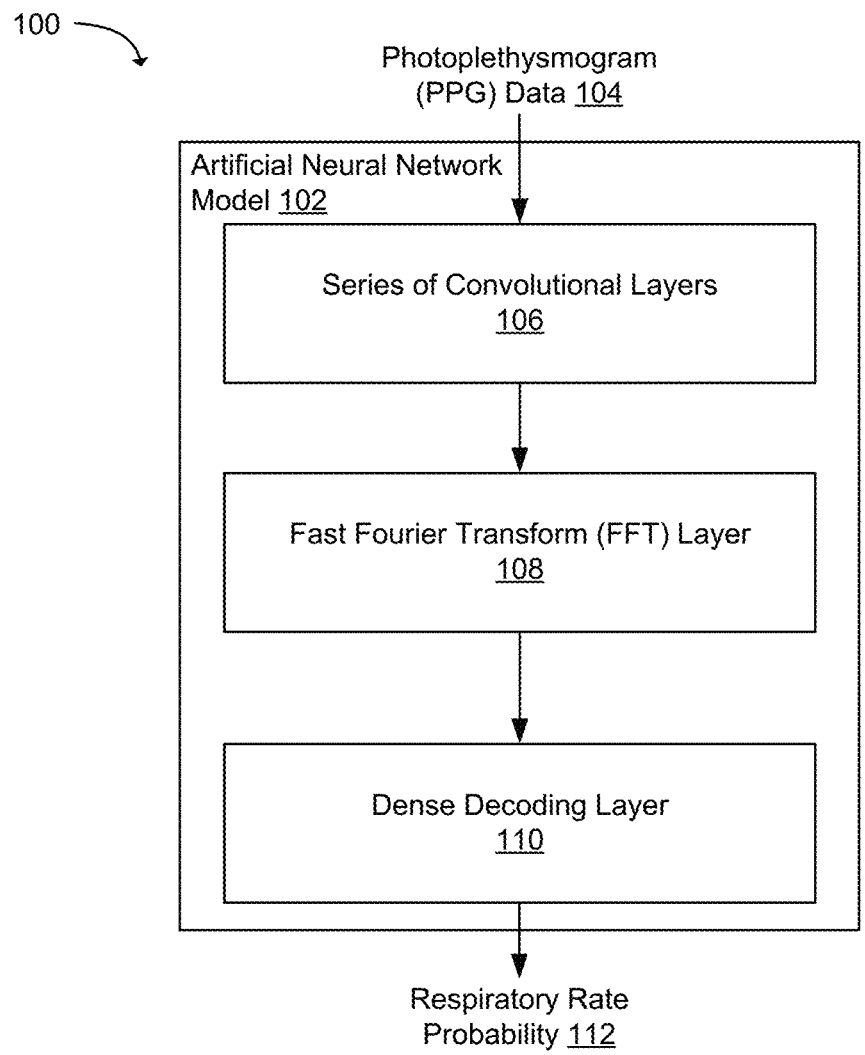
FIG. 1 is a block diagram illustrating an example of a processing system used to generate a respiratory rate probability.

To further describe the present technology, examples are now provided with reference to the figures. FIG. 1 is a block diagram illustrating a high-level example of a processing system 100 used to generate a respiratory rate probability. The processing system 100 includes an artificial neural network model 102 configured to extract a respiratory rate from PPG data. The artificial neural network model 102 (also referred to as the neural network model 102), in one example, is an end-to-end neural network having an architecture that includes a series of convolutional layers 106 followed by a fast Fourier transform (FFT) layer 108 and a dense decoding layer 110. As described in more detail below, PPG data 104 can be provided as input to the neural network model 102 and the architecture of the neural network model 102 can be configured to generate a respiratory rate probability 112 from the PPG data. PPG data can be obtained from a pulse oximeter device. Illustratively, a pulse oximeter sensor can be incorporated into a wearable device, such as a wrist worn device (e.g., smartwatch) or sock (e.g., smart sock), and the pulse oximeter may generate PPG data which can be obtained from the wearable device, and a respiratory rate prediction can be generated using the PPG data.

As illustrated, the architecture of the neural network model 102 includes a series of convolutional layers 106. The series of convolutional layers 106 can include any number of convolutional layers. In a specific example of the architecture of the neural network model 102, the series of convolutional layers 106 can include three convolutional layers. In some examples, the series of convolutional layers 106 may be a first convolutional layer that proceeds the FFT layer 108, and the architecture of the neural network model 102 can include a second series of convolutional layers (not shown) located between the FFT layer 108 and the dense decoding layer 110. The second series of convolutional layers may be similar to the first series of convolutional layers 106, but acts on a frequency transformed signal allowing the signal to be cleaned in the frequency domain potentially improving signal quality. For example, the second series of convolutional layers can be used to identify and remove artifacts from a Fourier transform output by the FFT layer 108, which may further improve a PPG signal.

The convolutional layers 106 of the neural network model 102 can be configured to identify a PPG signal in PPG data and remove artifacts contained in the PPG data. Respiratory rates can be detected in PPG data by measuring amplitude modulation, frequency modulation, and baseline wander. The convolutional layers 106 can be trained to ignore periodic patterns that are associated with the heart rate and instead highlight features such as amplitude modulation, frequency modulation, and baseline wander. Furthermore, the convolutional layers 106 can also be trained to determine the optimal combination of these internally-generated features with respect to an appropriate loss function. The PPG data can be obtained from a pulse oximeter monitor device. A PPG is an optically obtained plethysmogram used to detect blood volume changes in the microvascular bed of tissue of a subject. A pulse oximeter illuminates the skin and measures changes in light absorption to monitor the perfusion of blood to the dermis and subcutaneous tissue of the skin. The pulse oximeter detects a change in blood volume and measures an amount of light either transmitted or reflected to a photodiode. The pulse oximeter generates PPG data containing a PPG signal or waveform where each cardiac cycle appears as a peak in the PPG signal. The convolutional layers 106 of the neural network model 102 analyze PPG data obtained from the pulse oximeter to identify the PPG signal and remove artifacts (e.g., motion artifacts) from the PPG data.

The architecture of the neural network model 102 shown in FIG. 1 places the FFT layer 108 between the convolutional layer 106 and the dense decoding layer 110. The FFT layer 108 can be configured to apply a fast Fourier transform technique to the PPG signal output by the series of convolutional layers 106 to convert the PPG signal to a representation of a fundamental frequency and harmonic frequencies. Applying a fast Fourier transform technique to a PPG signal allows resulting PPG frequencies to be quantized into values that can be classified into respiratory rate values.

Placing the FFT layer 108 after the series of convolutional layers 106 and before the dense decoding layer 110 improves performance of predicting respiratory rates using the neural network model 102. In particular, applying a fast Fourier transform technique to a PPG signal output by the series of convolutional layers 106 reduces a number of parameters that are provided to the dense decoding layer 110 of the neural network model 102. By reducing the number of parameters provided as input to the dense decoding layer 110, an amount of data processed by the dense decoding layer 110 is decreased, which results in a shorter amount of time to generate respiratory rate probabilities 112.

Also, placing the FFT layer 108 after the series of convolutional layers 106 and before the dense decoding layer 110 improves accuracy of respiratory rate predictions output by the neural network model 102. More specifically, applying a fast Fourier transform technique to PPG signals output by the series of convolutional layers 106 allows PPG frequencies to be quantized, thereby restricting a number of possible PPG frequency values that can be classified as respiratory rate values. This allows for the use of classification as opposed to using regression, which can produce bias in the PPG data. As an example, using a means squared error technique as a loss function tends to pull values toward the mean, which creates bias in the PPG data. Using a fast Fourier transform technique reduces the chance of bias in the PPG data. For example, a fast Fourier transform technique allows PPG frequencies output by the FFT layer 108 to be classified as a probability distribution of respiratory rates, and allows for a maximum likelihood estimation to be applied to the probability distribution of respiratory rates to determine a respiratory rate probability 112.

The dense decoding layer 110 included in the neural network model 102 architecture can be configured to decode PPG frequency representations output by the FFT layer 108 into respiratory rate predictions. In one example, the dense decoding layer 110 decodes the PPG frequency representations into respiratory rate information (e.g., breaths per minute) used to generate a respiratory rate prediction. As an example, the dense decoding layer 110 selects a PPG frequency representation (e.g., a harmonic frequency) output by the FFT layer 108 and applies a mask to the PPG frequency representation which is used to visualize the PPG frequency representation as a respiratory rate value (e.g., 10, 12, or 15 breaths per minute). Thereafter, the respiratory rate values can be scored to create a probability distribution that indicates a maximum likelihood of a respiratory rate, which can be output as a respiratory rate probability 112. In one example, after scoring the respiratory rate values, the respiratory rate values can be input to a softmax layer (shown in FIG. 15) that has one neuron for each respiratory rate value. The softmax layer can normalize the respiratory rate values to sum to a value of one (1), creating a probability distribution of respiratory rate values that indicates a maximum likelihood of a respiratory rate value.

Figure 15:
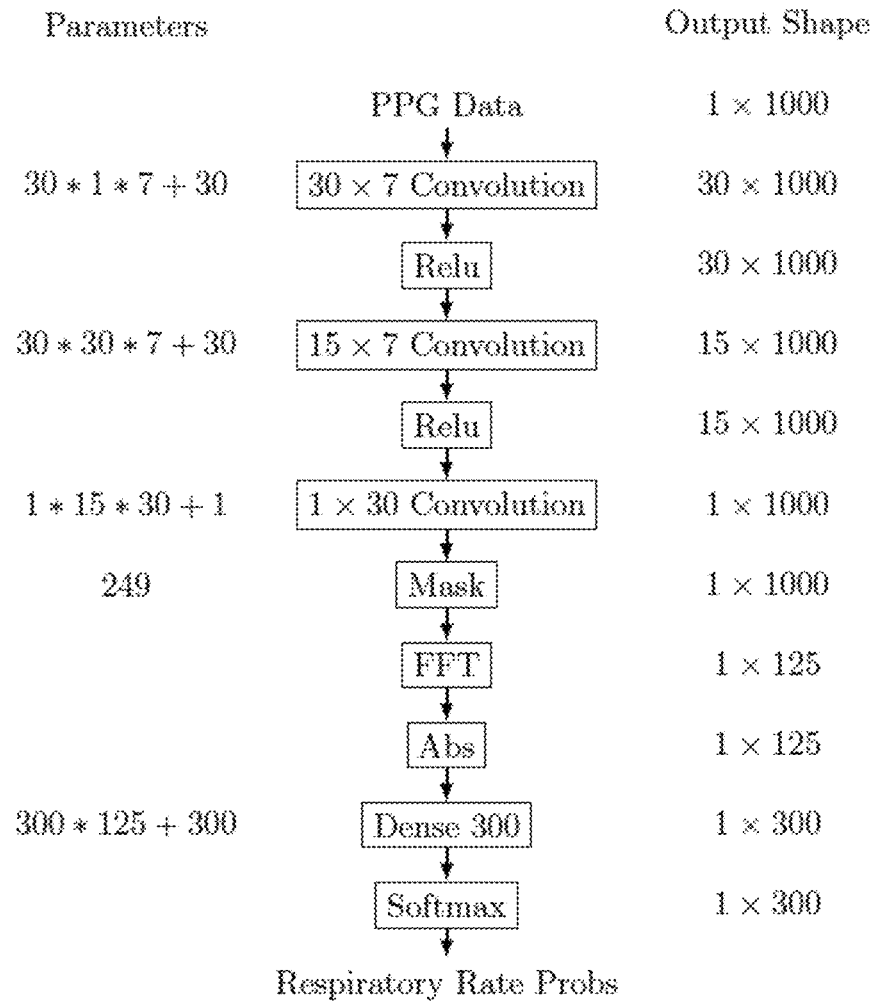
FIG. 15 is an illustration of an example end-to-end artificial neural network architecture.

The following example is an illustration of an end-to-end artificial neural network architecture configured to generate respiratory rate probabilities based on PPG data input. As will be appreciated, the example artificial neural network architecture shown in FIG. 15 is merely representative of a neural network architecture and is not meant to be limiting.

The neural network model 102 can be trained to generate respiratory rate probabilities using a training dataset of PPG data. The training data set can comprise PPG data collected from subjects using a pulse oximeter monitor. PPG data can be divided into a training dataset and a test dataset. In one example, the PPG data can be lowpass filtered at 12 Hz and down sampled to 25 Hz. Also, in one example, a peak detection function (e.g., a python scipy signals package) can be used to identify peak locations in a thoracic impedance respiration signal. These peak locations can be used to label individual breath peak locations on a PPG waveform. In one example, the neural network model 102 can be trained using categorical cross entropy to label PPG data in the training dataset to a respiratory rate category (e.g., number of breaths per minute categories) and an Adam optimizer to update weights assigned to the PPG data. As an illustration, the neural network model 102 can be trained for four (4) epochs using categorical cross entropy and the Adam optimizer. In another example, the neural network model 102 can be trained using binary cross entropy, mean squared error, least absolute deviation, or another appropriate loss function. Once the peak probabilities have been generated, they can be decoded into peak locations and respiratory rate using a variety of known peak detection methods. As will be appreciated, other techniques than those described above can be used to train the neural network model 102.

Respiratory rate probabilities 112 (also referred to as respiratory rate predictions) output by the neural network model 102 can be stored to a storage medium (e.g., RAM, hard-drive, and the like) included in a computing device (e.g., a wearable device) in order to make the respiratory rate probabilities 112 available in response to requests for the respiratory rate probabilities 112 (e.g., a request from an application or cloud service). In one example, a computing device that hosts the neural network model 102 can send respiratory rate probabilities 112 over a network (e.g., Internet, intranet, WAN, etc.) to another device (e.g., a mobile device, a server, etc.) in response to a request for the respiratory rate probabilities 112. Also, it is contemplated that a respiratory rate probability 112 can be displayed on a display of a wearable device.

The various processes and/or other functionality of the processing system 100 may be executed on one or more processors that are in communication with one or more memory modules. The processing system 100 may include one or more computing devices. In some examples, the processing system 100 can include a data store used to store PPG data 104 and/or respiratory rate probabilities 112 output by the neural network model 102. The term "data store" may refer to any device or combination of devices capable of storing, accessing, organizing and/or retrieving data. The storage system components of the data store may include storage systems such as volatile or non-volatile RAM, hard-drive type media, and a cloud storage network. The data store may be representative of a plurality of data stores as can be appreciated.

In some examples, the processing system 100 may include a network for transmitting data between servers, clients, and devices. The network may include any useful computing network, including an intranet, the Internet, a local area network, a wide area network, a wireless data network, or any other such network or combination thereof. Components utilized for such a system may depend at least in part upon the type of network and/or environment selected. Communication over the network may be enabled by wired or wireless connections and combinations thereof.

FIG. 1 illustrates that certain processing modules may be discussed in connection with this technology and these processing modules may be implemented as computing services. In one example configuration, a module may be considered a service with one or more processes executing on a server or other computer hardware. Such services may be centrally hosted functionality or a service application that may receive requests and provide output to other services or consumer devices. For example, modules providing services may be considered on-demand computing that are hosted in a server, virtualized service environment, grid or cluster computing system. An API may be provided for each module to enable a second module to send requests to and receive output from the first module. Such APIs may also allow third parties to interface with the module and make requests and receive output from the modules. While FIG. 1 illustrates an example of a system that may implement the techniques above, many other similar or different environments are possible. The example environments discussed and illustrated above are merely representative and not limiting.

Figure 2:
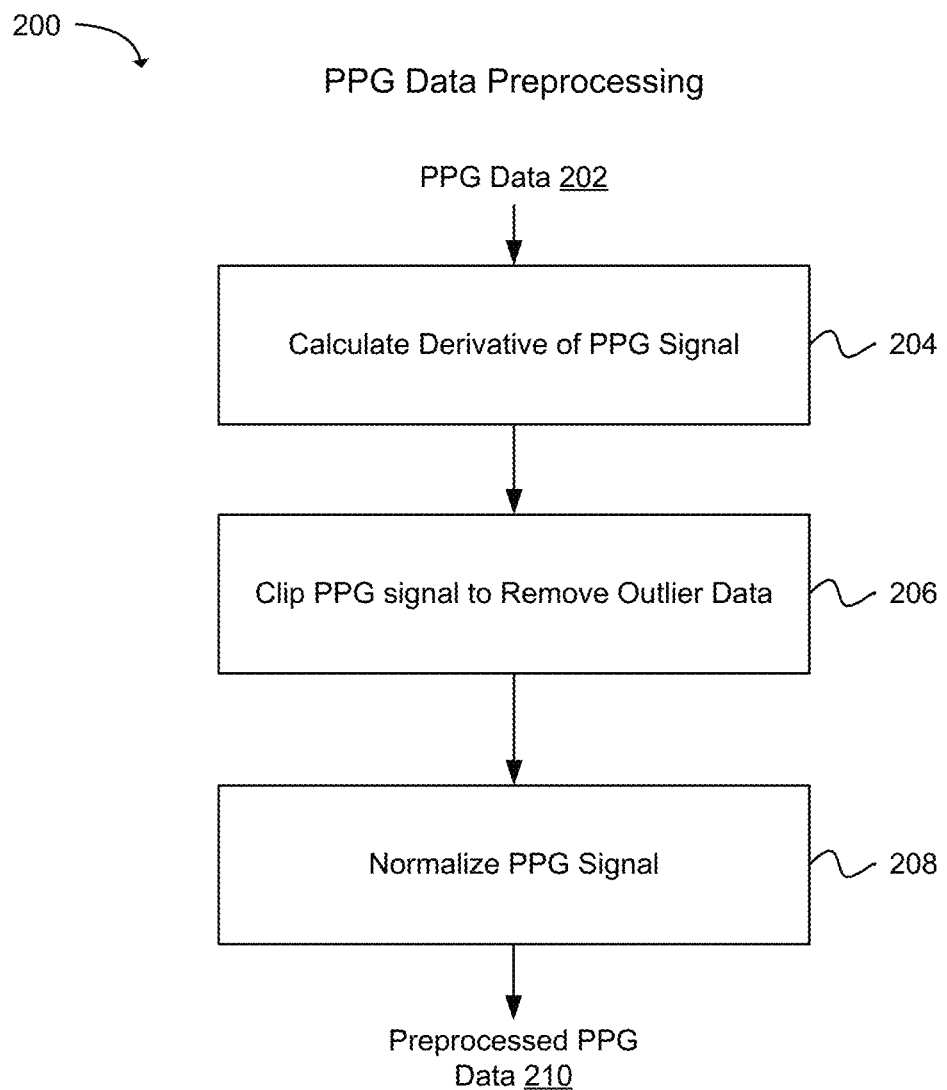
FIG. 2 is a flow diagram that illustrates an example method for preprocessing PPG data.

FIG. 2 is a flow diagram that illustrates an example method 200 for preprocessing PPG data 202. Prior to inputting PPG data 202 to the neural network model 102 described above, the PPG data 202 can be preprocessed to format the PPG data 202 for input to the neural network model 102. Preprocessing can be performed prior to training the neural network model 102 and prior to inference time in which a predicted respiratory rate value is generated. Also, PPG data 202 generated by a pulse oximeter sensor included in a wearable device (e.g., a smartwatch or smart sock) can be preprocessed prior to inputting the PPG data 202 to the neural network model 102.

Preprocessing of PPG data 202 can include one or more preprocessing steps. In one example, the preprocessing steps can include: (i) calculating a derivative of a PPG signal to accentuate high frequency components in the PPG signal, (ii) clipping the PPG signal to remove outlier data included in the PPG data, and (iii) normalizing the PPG signal to a predetermined standard deviation.

As in block 204, the preprocessing step of taking a derivative of the PPG signal can be performed to accentuate high frequency components in the PPG signal and diminish the effects of lower frequency motion artifacts. As in block 206, the preprocessing step of clipping the PPG signal can be performed to remove outlier data included in the PPG data 202. Outliers can be caused by movement and clipping can reduce the influence of the outliers in the PPG signal. In one example, clipping the PPG signal can include computing amplitude percentiles of the PPG signal and clipping values that are greater than a difference between amplitude percentiles. As an illustration, the 25th, 50th, and 75th amplitude percentiles of a PPG signal can be computed, and values can be clipped that are greater than six (6) times the difference between the 50th and 75th percentile of less than six (6) times the difference between the 50th percentile and the 25th percentile.

As in block 208, the preprocessing step of normalizing the PPG signal to a predetermined standard deviation can be performed to ensure that PPG signals included in PPG data 202 are approximately the same scale. After preprocessing the PPG data, the preprocessed PPG data 210 can be provided as input to the neural network model to generate respiratory rate probabilities as described earlier.

Figure 3:
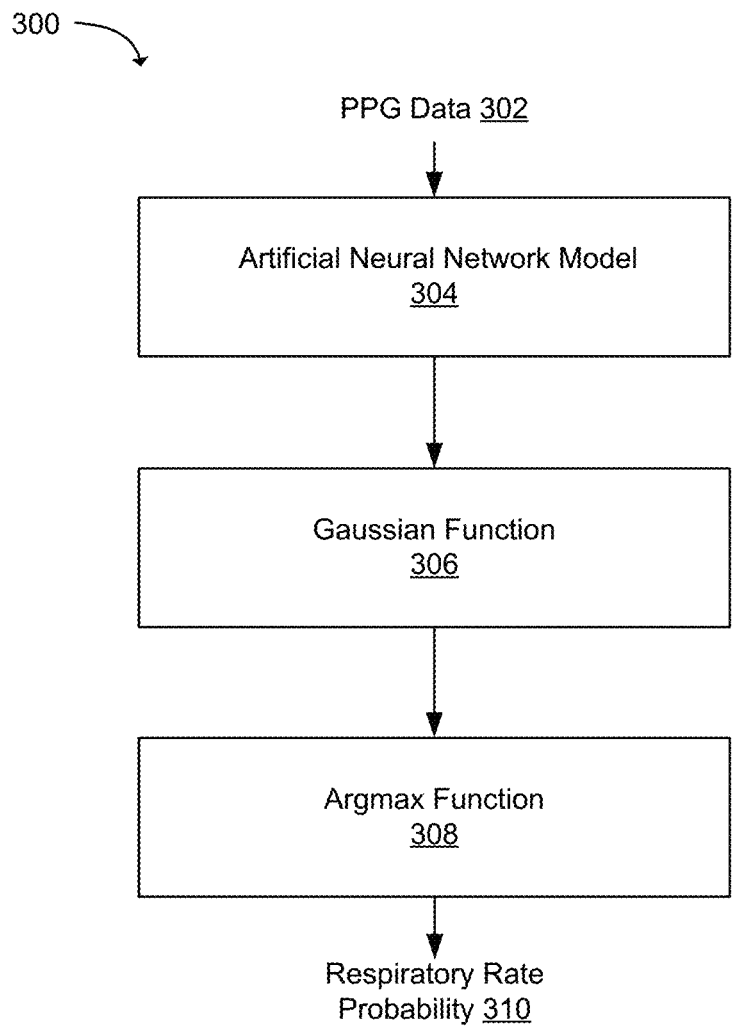
FIG. 3 is a block diagram illustrating an example processing system which can incorporate prior respiratory rate predictions to determine a respiratory rate probability.

FIG. 3 is a block diagram illustrating an example of a processing system 300 which can incorporate previous respiratory rate predictions to determine a respiratory rate probability 318. After training, the neural network model 102 described in association with FIG. 1 can be deployed to a production environment (e.g., a wearable device, a mobile device, a server, and the like) to infer respiratory rate values. The processing system 300 can incorporate prior predictions of respiratory rates into current predictions of respiratory rates at inference time. The prior predictions can be used to gauge whether a current prediction is reasonable. A prior respiratory rate prediction can be compared to a current respiratory rate prediction to determine whether a change in respiratory rate from the prior prediction to the current prediction is a data anomaly or is reasonable. Accordingly, a current respiratory rate prediction that is close to a previous respiratory rate prediction can be treated as being more likely accurate than current respiratory rate predictions that are far away from previous respiratory rate predictions.

In the example illustrated in FIG. 3, the processing system 300 can include an artificial neural network model 304 that accepts PPG data 302 as input. The artificial neural network model 304 can have the architecture described earlier in association with FIG. 1. In addition to the artificial neural network model 304, the processing system 300 can include a Gaussian function 306 and an argmax function 308. One or more prior respiratory rate predictions can be incorporated into a current respiratory rate prediction at inference time (i.e., at the time the neural network model 304 is used to generate a respiratory rate probability) by multiplying a probability distribution of respiratory rates output by the artificial neural network model 304 by the Gaussian function 306.

In one example, the Gaussian function 306 can have a mean value that is equal to the previous respiratory rate prediction. As an illustration, a respiratory rate distribution can be multiplied by the Gaussian function 306 with a standard deviation of five (5) breaths per minute and a mean value equal the most recent respiratory rate prediction. In one example, if there is no recent respiratory rate prediction available, the Gaussian function 306 can be replaced with an identity vector. The identity vector can be a vector of one (1) values of the same length as the Gaussian vector, resulting in not modifying the input to the argmax function 308 described below. In another example where no recent respiratory rate prediction is available, the Gaussian function 306 step described above may not be performed, and the argmax function 308 described below can be applied to the probability distribution After multiplying the probability distribution by the Gaussian function 306, an argmax function 308 (arguments of the maxima) can be used to produce the respiratory rate probability 310. For example, an argmax of the respiratory rate distribution can be calculated to produce the respiratory rate probability 310. The probability of the respiratory rate value can be used as a quality indicator for respiratory rate values. Respiratory rates with low probability may be rejected to avoid false respiratory rate readings.

Figure 4:
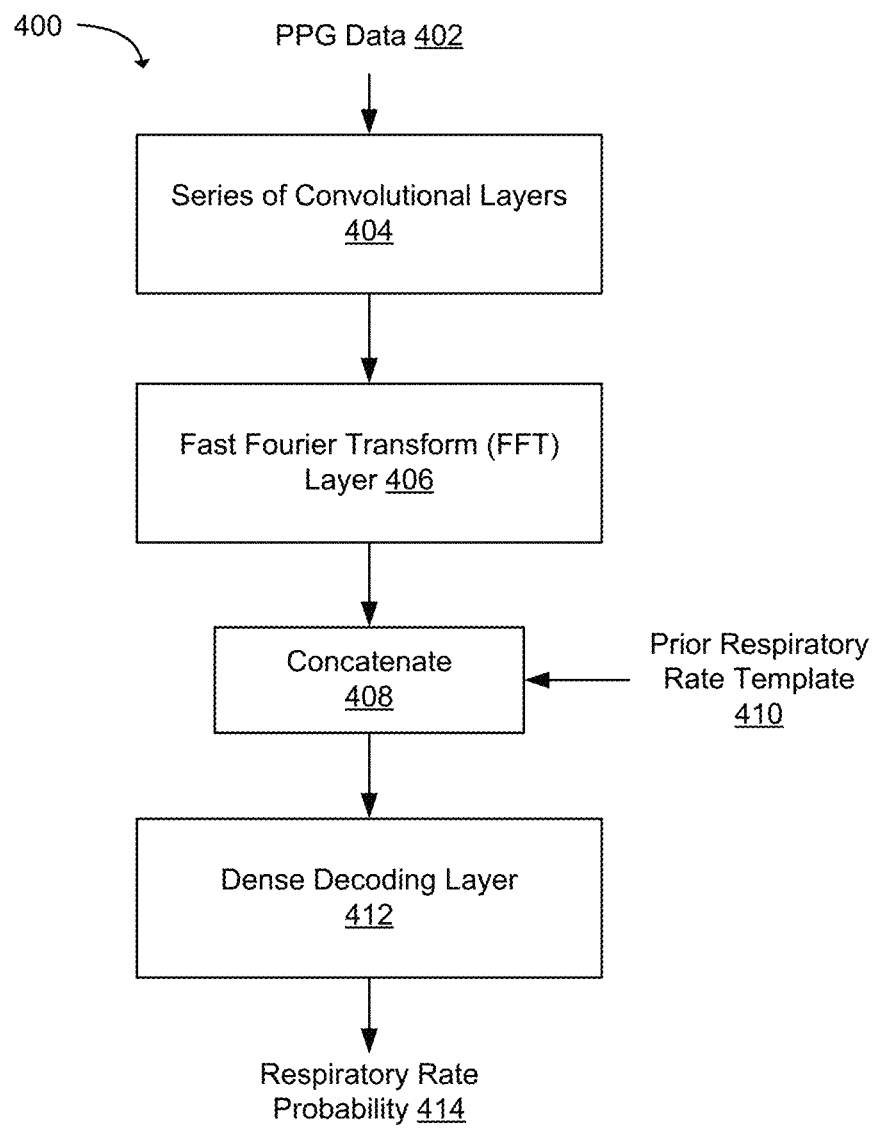
FIG. 4 is a block diagram illustrating an example network architecture for an artificial neural network model which incorporates prior respiratory rate information to generate a respiratory rate probability.

FIG. 4 is a block diagram that illustrates an example network architecture for an artificial neural network model 400 that incorporates prior respiratory rate information to generate a respiratory rate probability 414. In the discussion above, the processing system 300 incorporated prior respiratory rate information after generating a probability distribution of respiratory rates. The network architecture shown in FIG. 4 incorporates prior respiratory rate information into the neural network model 400 to allow training of the neural network model 400 to include the prior respiratory rate information.

Prior predictions of respiratory rates can be used as part of generating a current respiratory rate probability in a number of ways. In one example, a series of sine waves corresponding to a fundamental frequency and harmonic frequencies of a prior respiratory rate prediction can be summed. The resulting sum provides a prior respiratory rate template 410 which can be passed to the neural network model 400. One method that can be used to pass a prior respiratory rate template 410 to the neural network model 400 includes concatenating a Fourier transform of the prior respiratory rate template 410 to the Fourier transform output by the FFT layer 406 of the neural network model 400. As an illustration, PPG data 402 included in a training dataset can be input to a series of convolutional layers 404 to remove artifacts and clean up the PPG signal. The FFT layer 406 can be applied to the PPG signal to produce a Fourier transform of the PPG signal. A Fourier transform of a prior respiratory rate template 410 can be produced, and the Fourier transform of a prior respiratory rate template 410 can be concatenated 408 to the Fourier transform of the PPG signal. The resulting concatenated Fourier transform comprising PPG frequency representations of the PPG data 402 and the prior respiratory rate template 410 can be input to a dense decoding layer 412 of the neural network model 400. The dense decoding layer 412 decodes the PPG frequency representations, as described earlier in association with FIG. 1, and outputs a respiratory rate probability 414.

Figure 16:
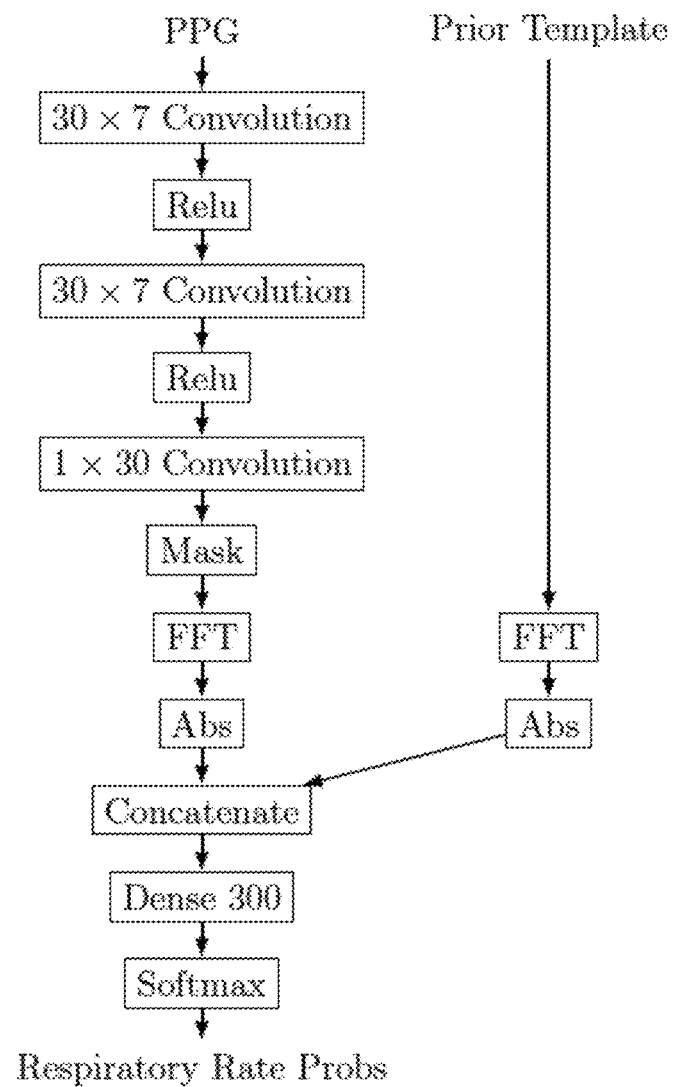
FIG. 16 is an illustration of an example end-to-end artificial neural network architecture with prior respiratory rate information.

The following example illustrates an end-to-end artificial neural network architecture configured to generate incorporate prior respiratory rate information into an artificial neural network model to generate a respiratory rate probability. As will be appreciated, the example artificial neural network architecture shown in FIG. 16 is merely representative of a neural network architecture and is not limiting.

Figure 5:
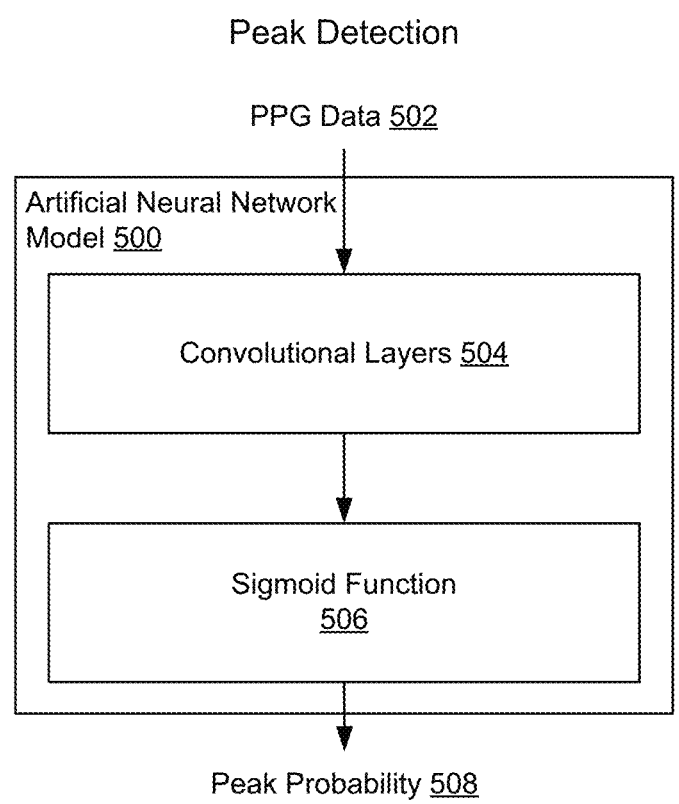
FIG. 5 is a block diagram that illustrates an example artificial neural network model configured to generate peak probabilities that correspond to individual respiratory rate peaks which can be decoded to produce a final respiratory rate prediction.
Figure 17:
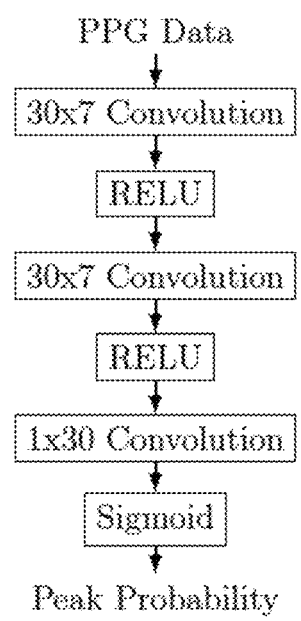
FIG. 17 is an illustration of an example peak detection neural network.

FIG. 5 is a block diagram that illustrates an example artificial neural network model 500 configured to generate peak probabilities 508 that correspond to individual respiratory rate peaks which can be decoded to produce a final respiratory rate prediction. For example, peak probabilities 508 can be decoded using peak detection to produce a final respiratory rate probability. In one example, a peak detection method can use the preprocessing technique described above in association with FIG. 2 to preprocess PPG data 502. Following preprocessing, a PPG signal can be passed to the neural network model 500 in short windows (e.g., 100, 125, or 150 samples). The neural network model 500 can include of a series of convolutional layers 504 with a sigmoid function 506 output corresponding to a peak probability 508. FIG. 17 illustrates an artificial neural network architecture configured to generate a peak probability. As will be appreciated, the example artificial neural network architecture shown in FIG. 17 is merely representative and is not meant to be limiting.

Figure 6:
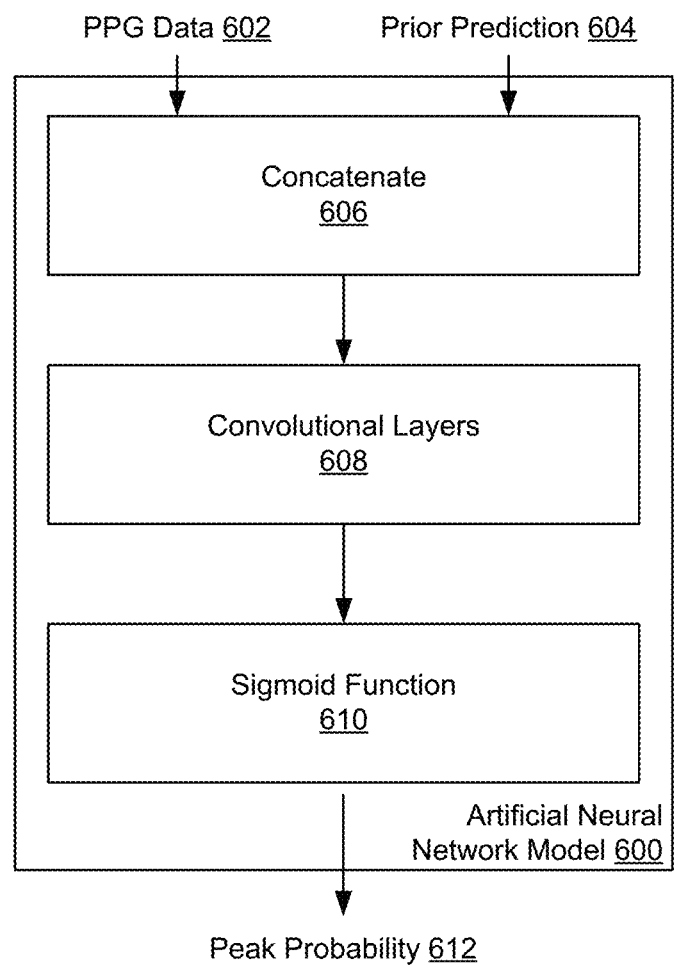
FIG. 6 is a block diagram illustrating an example artificial neural network model trained using prior respiratory rate predictions.
Figure 18:
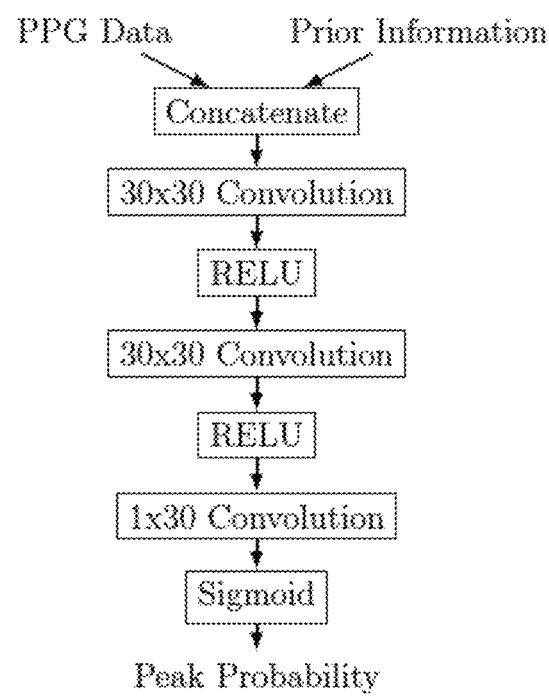
FIG. 18 is an illustration of an example peak detection neural network using prior prediction information.

FIG. 6 is a block diagram illustrating an example artificial neural network model 600 trained using prior respiratory rate predictions. The neural network model 600 can be trained using binary cross entropy, mean squared error, least absolute deviation, or another appropriate loss function. The neural network model 600 can include a concatenate layer 606, a series of convolutional layers 608, and a sigmoid function 610 layer. After peak probabilities have been generated, the peak probabilities can be decoded into peak locations and respiratory rate using a variety of known peak detection methods. The neural network model 600 can be provided with information from prior respiratory rate predictions (e.g., a prior prediction 604 input). For example, the expected location of the next peak can be passed to the neural network model 600 in addition to PPG data 602. One example of passing prior predictions 604 to the neural network model 600 includes adding an additional input channel that is the same length as the PPG signal, where the input channel has a value of one (1) when the value of the next respiratory rate is expected to be zero (0). The neural network model 600 can learn to incorporate the prior prediction 604 to improve prediction accuracy. FIG. 18 illustrates passing prior prediction information to neural network model. As described earlier, the peak probabilities can be decoded into peak locations and a respiratory rate using a variety of known peak detection methods.

Figure 7:
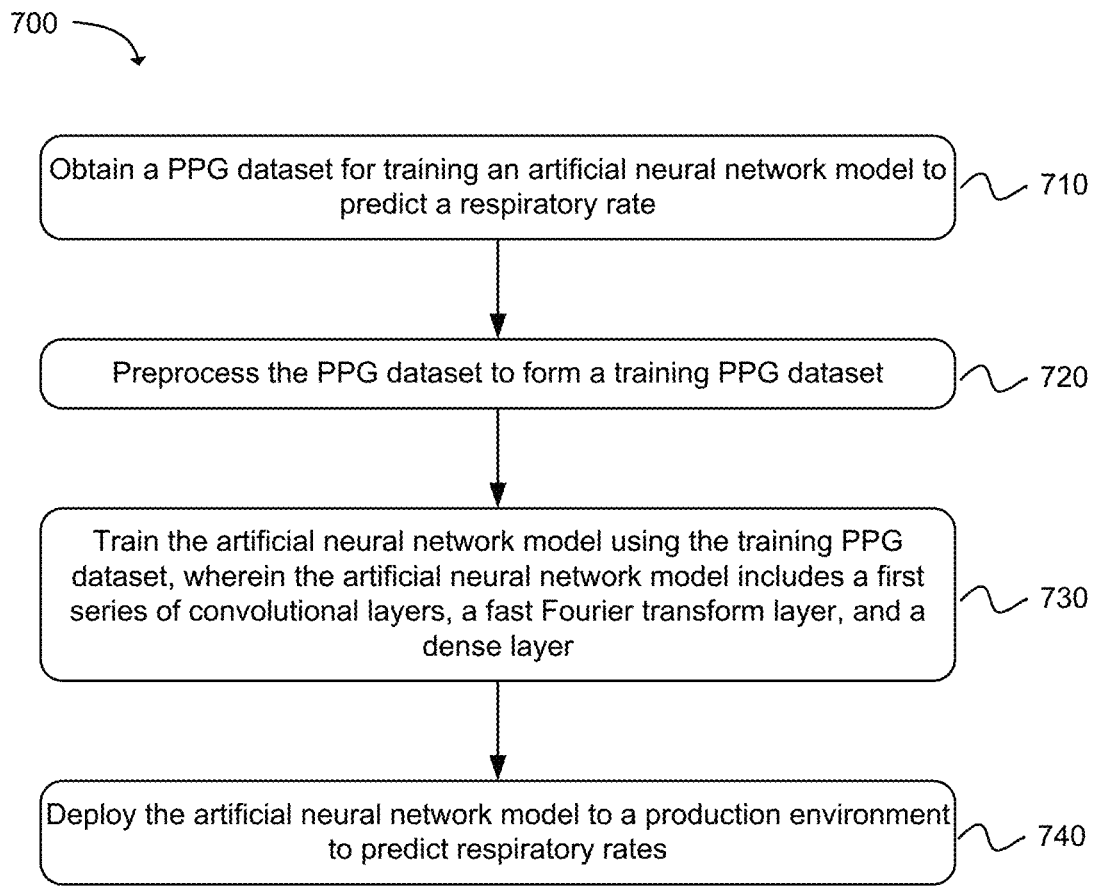
FIG. 7 is a flow diagram that illustrates an example method for training an artificial neural network model to predict a respiratory rate from a PPG signal.

FIG. 7 is a flow diagram illustrating an example method 700 for training an artificial neural network model to generate a respiratory rate prediction from a PPG signal. As in block 710, a PPG dataset can be obtained for training the artificial neural network model. Prior to training the artificial neural network model, the PPG dataset can be preprocessed, as in block 720. Preprocessing the PPG dataset can include (i) calculating a derivative of the PPG signal to accentuate high frequency components, (ii) clipping the PPG signal to remove outlier data included in the PPG dataset, and (iii) normalizing a PPG signal to a predetermined standard deviation.

As in block 730, the artificial neural network model can be trained using the training PPG dataset. The artificial neural network model can include a first series of convolutional layers to identify a PPG signal in PPG data and remove artifacts contained in the PPG data, a fast Fourier transform (FFT) layer to convert the PPG signal to PPG frequency representations, and a dense layer to decode the PPG frequency representations to respiratory rate predictions. In one example, an output layer of the neural network model is a softmax layer that has an output neuron for each respiratory rate value. In one example, the artificial neural network model can be trained using categorical cross entropy to label the PPG data in the training dataset as a respiratory rate category, and an Adam optimizer to update weights assigned to the PPG data. In some examples, prior respiratory rate information can be used to train the artificial neural network model. For example, a prior respiratory rate template can be generated by summing a series of sine waves that correspond to a fundamental frequency of a prior respiratory rate prediction and a harmonic of the prior respiratory rate prediction, and the prior respiratory rate template can be input to the artificial neural network model during training of the artificial neural network model. Inputting a prior respiratory rate prediction to the artificial neural network model during training can include (i) calculating a Fourier transform of a prior respiratory rate prediction, (ii) concatenating the Fourier transform of the prior respiratory rate prediction to a Fourier transform output by the FFT layer to form a concatenated Fourier transform, and (iii) providing the concatenated Fourier transform to the dense layer of the artificial neural network model.

After training the artificial neural network model, the artificial neural network model can be deployed to a production environment to predict respiratory rates, as in block 740. For example, the artificial neural network model can be deployed to a wearable device (e.g., a smartwatch or smart sock), a mobile device, a server in a service provider computing environment (e.g., a cloud environment), etc. After deploying the artificial neural network to a production environment, PPG data generated by a pulse oximeter sensor or monitor can be input to the artificial neural network model, and the artificial neural network model can analyze the PPG data to determine a respiratory rate prediction.

Figure 8:
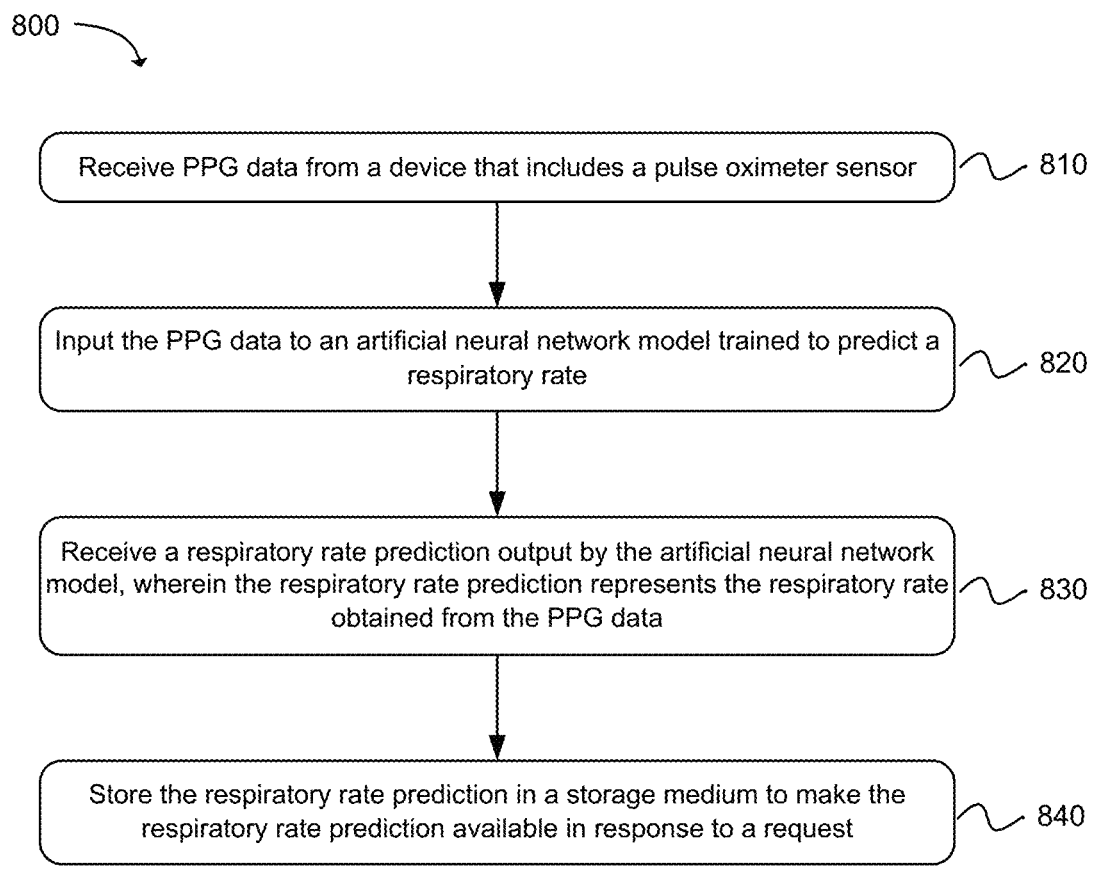
FIG. 8 is a flow diagram that illustrates an example method for obtaining a respiratory rate prediction from an artificial neural network model.

FIG. 8 is a flow diagram that illustrates an example method 800 for obtaining a respiratory rate prediction from a photoplethysmogram. As in block 810, PPG data can be received from a device that includes a pulse oximeter sensor, such as a wearable device. The device may be one of many physical electronic devices that create a large network of addressable devices. The devices may be part of a "network" that is commonly referred to as the Internet of Things (IoT). The devices that make up the network may be addressable over a wireless network, such as WI-FI, Zigbee, Z-Wave, BLUETOOTH, NFC (Near Field Communication), cellular, and the like.

In one example, the PPG data received from the device can be preprocessed prior to inputting the PPG data to the artificial neural network. For example, preprocessing the PPG data can include one or more of: calculating a derivative of the PPG signal to accentuate high frequency components, clipping the PPG signal to remove outlier data included in the PPG dataset, and/or normalizing a PPG signal to a predetermined standard deviation.

As in block 820, the PPG data can be input to an artificial neural network model trained to predict a respiratory rate, as described earlier. The artificial neural network model can include: a first series of convolutional layers to identify a PPG signal in the PPG data and remove artifacts contained in the PPG data, a fast Fourier transform (FFT) layer to convert the PPG signal to PPG frequency representations, and a dense layer to decode the PPG frequency representations to respiratory rate predictions.

In one example, a previous respiratory rate prediction output by the artificial neural network model can be obtained, and the previous respiratory rate prediction can be compared to a current respiratory rate prediction output by the artificial neural network model to determine whether the current respiratory rate prediction is within a quality threshold of the previous respiratory rate prediction. For example, the previous respiratory rate prediction can be compared to the current respiratory rate prediction by (i) generating a respiratory rate distribution, wherein the current respiratory rate prediction is multiplied by a Gaussian function that has a mean value that is equal to the previous respiratory rate prediction, and (ii) calculating an argmax of the respiratory rate distribution to produce the respiratory rate prediction. In the case that a previous respiratory rate prediction is unavailable, a respiratory rate distribution can be generated by multiplying a current respiratory rate prediction by an identity vector, and calculating an argmax of the respiratory rate distribution to produce the respiratory rate prediction.

As in block 830, output of a respiratory rate prediction can be received from the artificial neural network model. The respiratory rate prediction can represent the respiratory rate obtained from the PPG signal. In one example, the respiratory rate prediction can be evaluated based on previous respiratory rate predictions output by the artificial neural network model to determine a probability that the respiratory rate prediction is accurate, and the respiratory rate prediction can be discarded when the probability is low that the respiratory rate prediction is accurate.

As in block 840, the respiratory rate prediction can be stored in a storage medium (e.g., RAM, hard-drive, flash memory, etc.) to make the respiratory rate prediction available in response to a request from an application, program, service, process, and the like. It is contemplated that the respiratory rate prediction output by the artificial neural network model can be sent over a network to a device, such as a mobile device or server, in response to a request for the respiratory rate prediction. In one example, the respiratory rate prediction can be pushed to another device, such as a mobile device or server, using a push protocol. For example, the device may be configured to communicate with other computing devices using either TCP (Transmission Control Protocol) or UDP (User Datagram Protocol) protocols. Likewise, the device may be programmed to communicate with other computing devices using any suitable protocol including, for example, MQTT (Message Queue Telemetry Transport), CoAP (Constrained Application Protocol), HTTP (Hypertext Transfer Protocol), and HTTPS (HTTP secure). For example, some devices may transport data using TCP, while others may communicate data using UDP. Some devices may use MQTT, while others may use CoAP, and still others may use HTTPs. It is also contemplated that the respiratory rate prediction can be displayed on the display of a wearable device that hosts the artificial neural network model.

Figure 9:
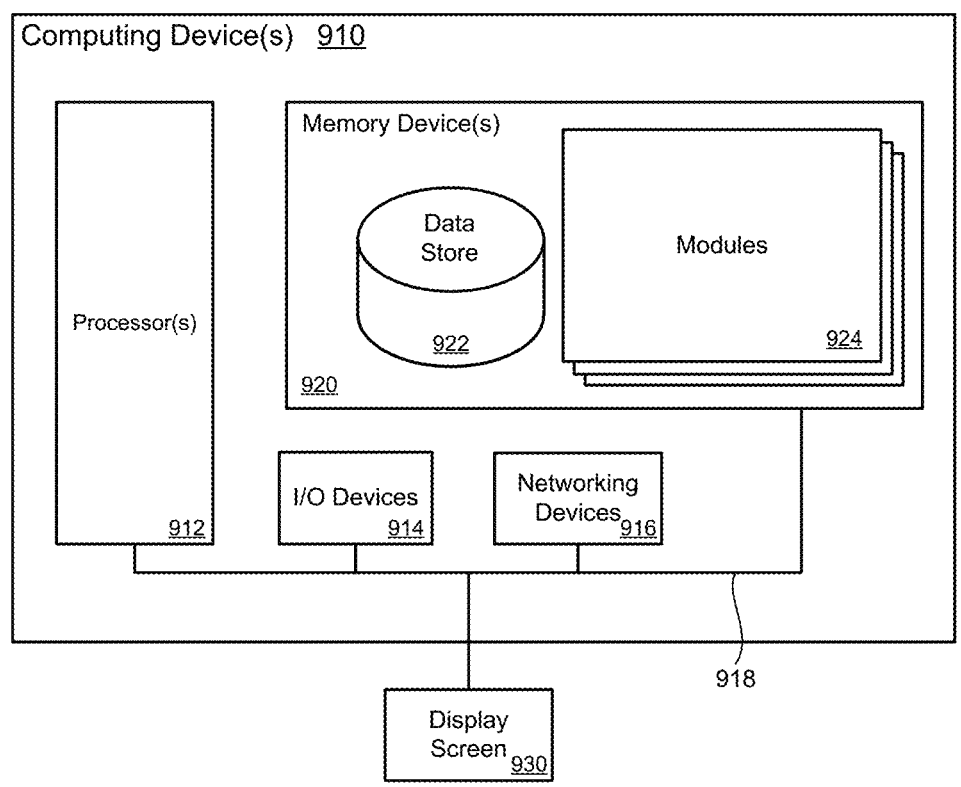
FIG. 9 is a block diagram illustrating an example of a computing device that may be used to execute a method for obtaining a respiratory rate prediction from an artificial neural network model.
Figure 10:
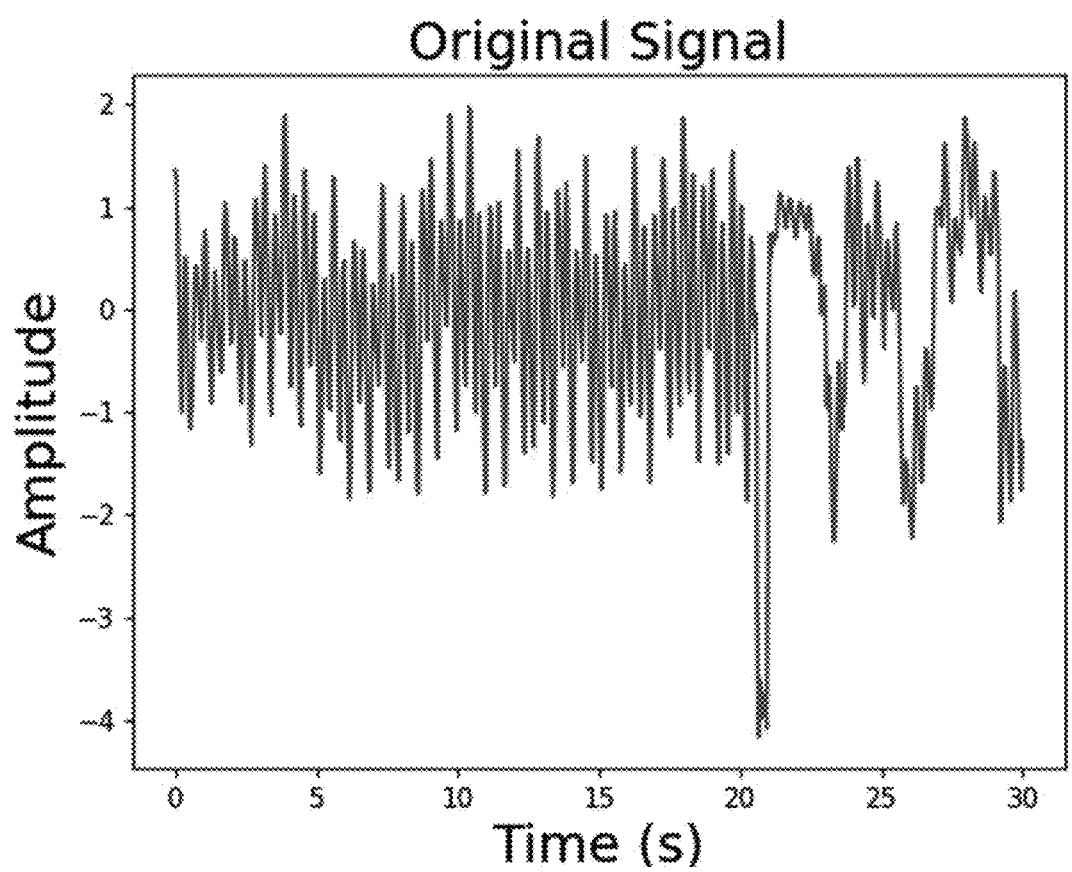
FIG. 10 is an illustration of what a photoplethysmogram signal looks like at various processing stages.
Figure 11:
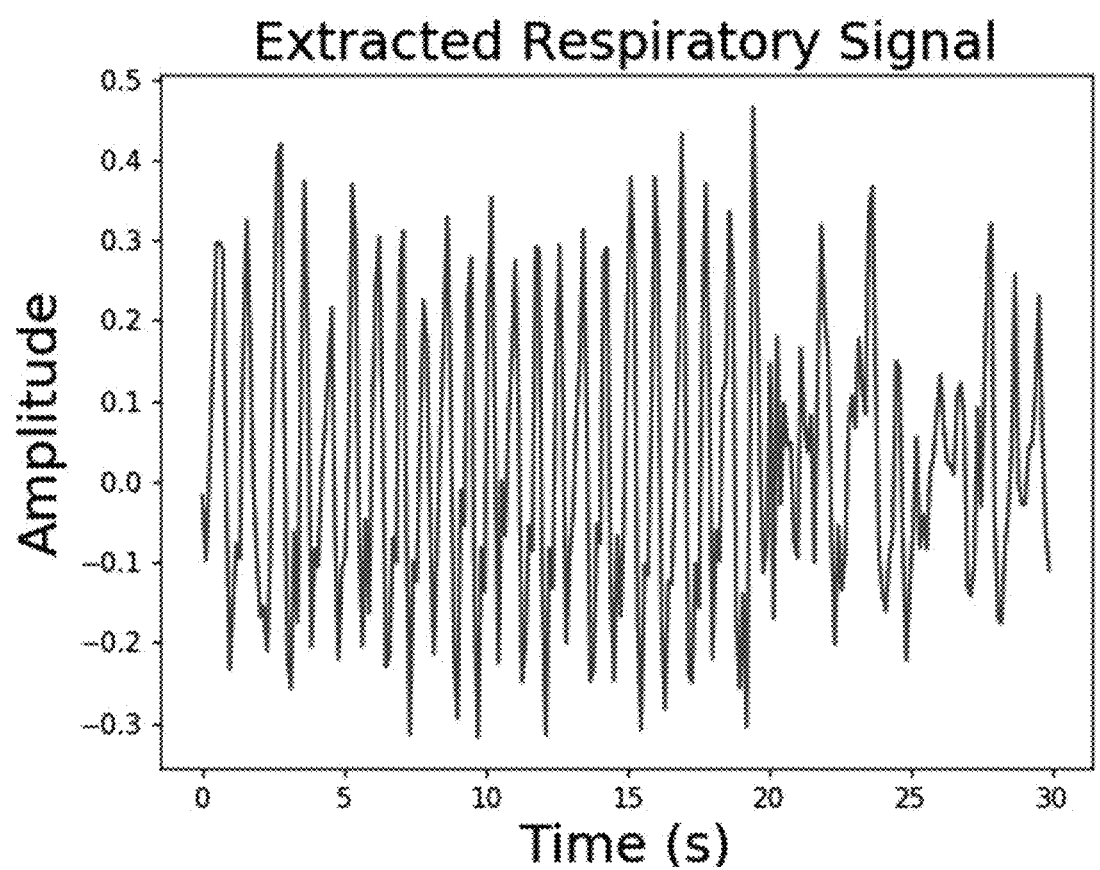
FIG. 11 is an illustration showing the extracted respiratory signal and the fast Fourier transform of the photoplethysmogram signal.
Figure 12:
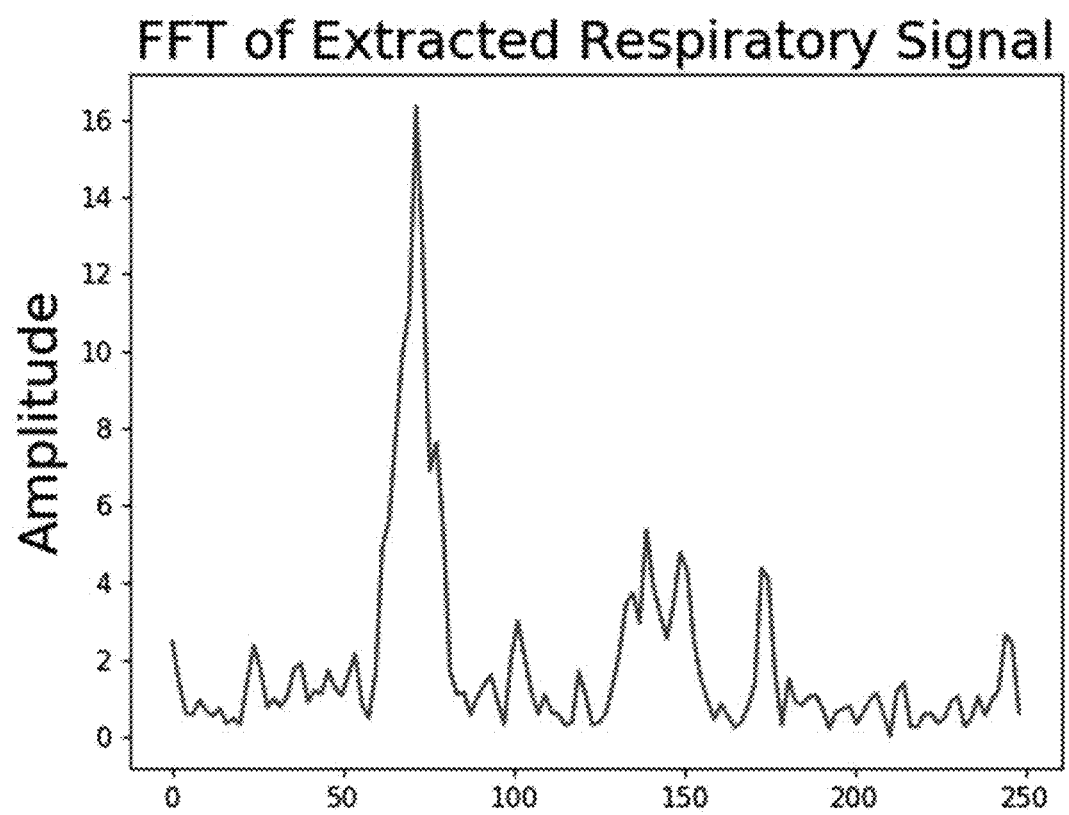
FIG. 12 is another illustration showing the extracted respiratory signal and the fast Fourier transform of the photoplethysmogram signal.

FIG. 9 illustrates a computing device 910 on which modules of this technology may execute. A computing device 910 is illustrated on which a high-level example of the technology may be executed. The computing device 910 may include one or more processors 912 that are in communication with memory devices 920. The computing device 910 may include a local communication interface 918 for the components in the computing device 910. For example, the local communication interface 918 may be a local data bus and/or any related address or control busses as may be desired.

The memory device 920 may contain modules 924 that are executable by the processor(s) 912 and data for the modules 924. The modules 924 can include convolutional modules, fast Fourier transform modules, dense decoding modules, and other modules. The modules 924 may execute the functions described earlier. A data store 922 may also be located in the memory device 920 for storing data related to the modules 924 and other applications along with an operating system that is executable by the processor(s) 912.

Other applications may also be stored in the memory device 920 and may be executable by the processor(s) 912. Components or modules discussed in this description can be implemented in the form of software using high-level programming languages that are compiled, interpreted or executed using a hybrid of the methods.

The computing device 910 may also have access to I/O (input/output) devices 914 that are usable by the computing device 910. One example of an I/O device is a display screen 930 that is accessible to the computing device 910. Networking devices 916 and similar communication devices may be included in the computing device 910. The networking devices 916 may be wired or wireless networking devices that connect to the internet, a LAN, WAN, or other computing network.

The components or modules that are shown as being stored in the memory device 920 may be executed by the processor(s) 912. The term "executable" may mean a program file that is in a form that may be executed by a processor 912. For example, a program in a higher level language may be compiled into machine code in a format that may be loaded into a random access portion of the memory device 920 and executed by the processor 912, or source code may be loaded by another executable program and interpreted to generate instructions in a random access portion of the memory to be executed by a processor. The executable program may be stored in any portion or component of the memory device 920. For example, the memory device 920 may be random access memory (RAM), read only memory (ROM), flash memory, a solid state drive, memory card, a hard drive, optical disk, floppy disk, magnetic tape, or any other memory components.

The processor 912 may represent multiple processors and the memory device 920 may represent multiple memory units that operate in parallel to the processing circuits. This may provide parallel processing channels for the processes and data in the system. The local communication interface 918 may be used as a network to facilitate communication between any of the multiple processors and multiple memories. The local communication interface 918 may use additional systems designed for coordinating communication such as load balancing, bulk data transfer and similar systems.

Figure 13:
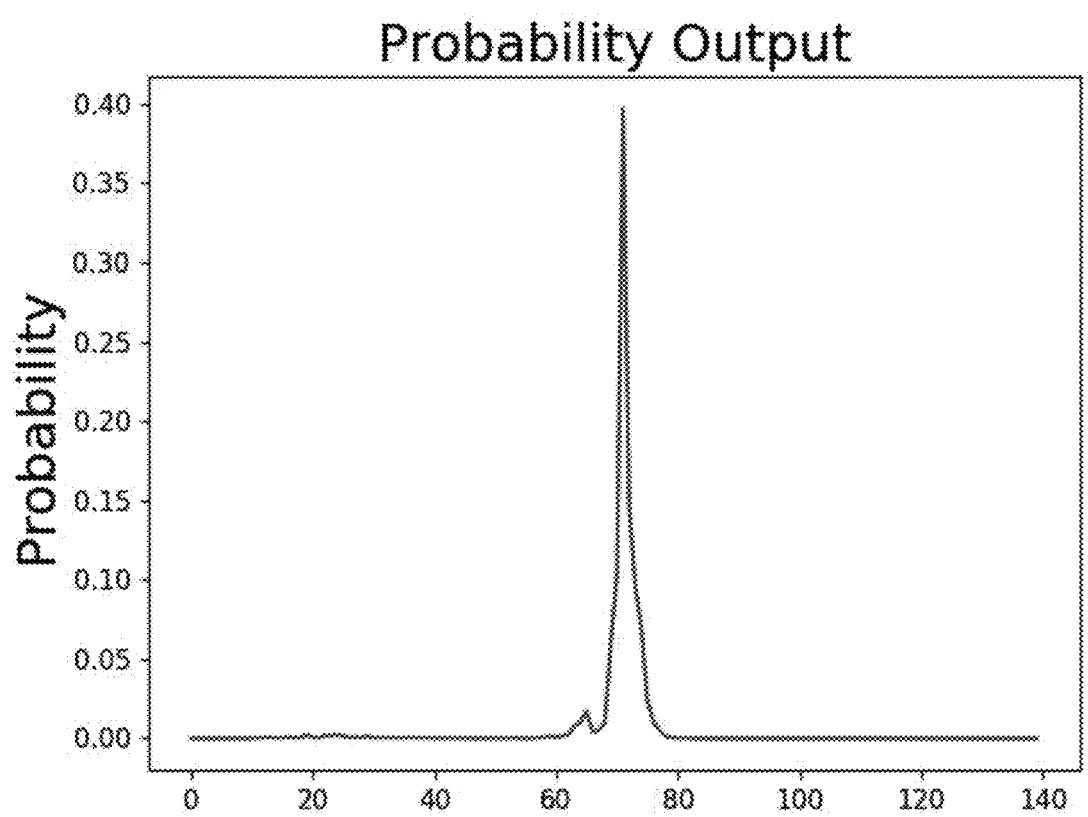
FIG. 13 is an illustration of the final respiratory rate probability output of the neural network.

As shown in FIGS. 13, the PPG data is substantially cleaner as compared to the PPG data shown in the preceding examples, and the FFT has a clear peak at the respiratory rate value (approximately 71 breaths per minute). The FFT can be more easily decoded by the dense decoding layer of the artificial neural network model. Again there is a clear peak in probability at the correct respiratory rate value.

Figure 14:
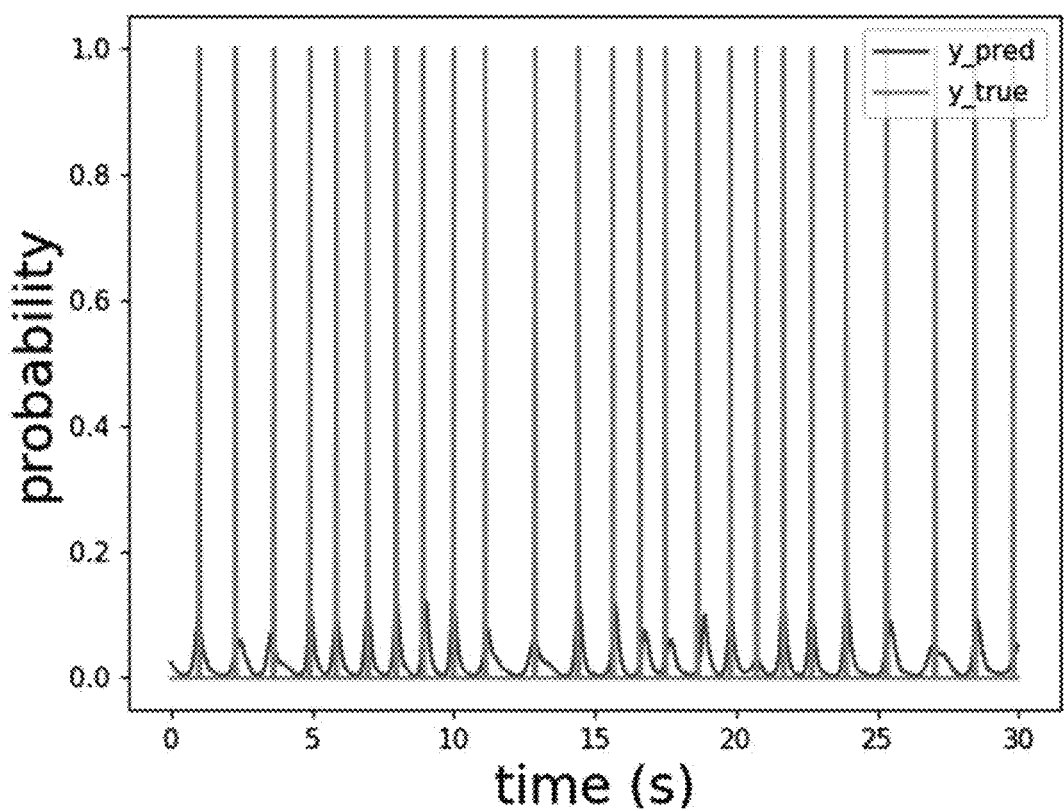
FIG. 14 is an illustration of peak probability output of peak detection neural network model.

FIG. 14 shows an example peak detection neural network. In particular, shown are peak probabilities output from the neural network model described herein over time. The darker label shows the probabilities. The lighter vertical lines show the true peak locations. As can be seen, the peaks match well with the labels.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions and may even be distributed over several different code segments, among different programs and across several memory devices. Similarly, operational data may be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, a non-transitory machine readable storage medium, such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

What is claimed is:

1. A system for predicting a respiratory rate from a photoplethysmogram (PPG), the system comprising:
   at least one processor; and
   a memory device including instructions that, when executed by the at least one processor, cause the system to:
      input PPG data to an artificial neural network model trained to predict a respiratory rate using the PPG data,
      wherein the artificial neural network model includes:
         a first series of convolutional layers to identify a PPG signal in the PPG data and remove artifacts contained in the PPG data,
         a fast Fourier transform (FFT) layer to convert the PPG signal to PPG frequency representations, the FFT layer positioned after the first series of convolutional layers, and
         a dense layer to decode the PPG frequency representations to respiratory rate predictions, the dense layer positioned after the FFT layer;
      receive a respiratory rate prediction output by the artificial neural network model,
      wherein the respiratory rate prediction represents the respiratory rate contained in the PPG data; and
      provide the respiratory rate prediction.

2. The system as recited in claim 1, wherein the memory device further includes instructions that, when executed by the at least one processor, cause the system to preprocess the PPG data, wherein preprocessing includes (i) calculating a derivative of the PPG signal to accentuate high frequency components in the PPG data, (ii) clipping the PPG signal to remove outlier data included in the PPG data, and (iii) normalizing a PPG waveform of the PPG signal to a predetermined standard deviation.

3. The system as recited in claim 1, wherein the artificial neural network model is trained using: categorical cross entropy to label the PPG data in a training dataset as a respiratory rate category, and an Adam optimizer to update weights assigned to the PPG data.

4. The system as recited in claim 1, wherein the memory device further includes instructions that, when executed by the at least one processor, cause the system to:
   generate a prior respiratory rate template by summing a series of sine waves that correspond to a fundamental frequency of a prior respiratory rate prediction and a harmonic of the prior respiratory rate prediction; and
   input the prior respiratory rate template to the artificial neural network model during training of the artificial neural network model.

5. The system as recited in claim 4, wherein inputting the prior respiratory rate prediction to the artificial neural network model during training further comprises:
   calculating a Fourier transform of the prior respiratory rate prediction;
   concatenating the Fourier transform of the prior respiratory rate prediction to a Fourier transform output by the FFT layer to form a concatenated Fourier transform; and
   providing the concatenated Fourier transform to the dense layer of the artificial neural network model.

6. The system as recited in claim 1, wherein the first series of convolutional layers comprises three convolutional layers.

7. The system as recited in claim 1, wherein an output layer of the artificial neural network model is a softmax layer that has an output neuron for each respiratory rate value.

8. The system as recited in claim 1, wherein the artificial neural network model further includes a second series of convolutional layers between the FFT layer and the dense layer to remove artifacts from a Fourier transform output by the FFT layer.

9. The system as recited in claim 1, wherein the memory device further includes instructions that, when executed by the at least one processor, cause the system to:
obtain a previous respiratory rate prediction output by the artificial neural network model; and
compare the previous respiratory rate prediction to a current respiratory rate prediction output by the artificial neural network model to determine whether the current respiratory rate prediction is within a quality threshold of the previous respiratory rate prediction.

10. The system as recited in claim 9, wherein comparing the previous respiratory rate prediction to the current respiratory rate prediction further comprises:
generating a respiratory rate distribution, wherein the current respiratory rate prediction is multiplied by a Gaussian function that has a mean value that is equal to the previous respiratory rate prediction; and
calculating an argmax of the respiratory rate distribution to produce the respiratory rate prediction.

11. The system as recited in claim 1, wherein the memory device further includes instructions that, when executed by the at least one processor, cause the system to:
determine that a previous respiratory rate prediction output by the artificial neural network model is unavailable;
generate a respiratory rate distribution by multiplying a current respiratory rate prediction by an identity vector; and
calculate an argmax of the respiratory rate distribution to produce the respiratory rate prediction.

12. The system as recited in claim 1, wherein the memory device further includes instructions that, when executed by the at least one processor, cause the system to:
evaluate the respiratory rate prediction based on previous respiratory rate predictions output by the artificial neural network model to determine a probability that the respiratory rate prediction is accurate; and
discard the respiratory rate prediction when the probability is low that the respiratory rate prediction is accurate.

13. A computer implemented method for obtaining respiratory rate predictions from photoplethysmograms, comprising:
receiving photoplethysmogram (PPG) data from a device that includes a pulse oximeter sensor;
inputting the PPG data to an artificial neural network model trained to predict a respiratory rate,
wherein the artificial neural network model includes:
(i) a first series of convolutional layers to identify a PPG signal in the PPG data and remove artifacts contained in the PPG data,
(ii) a fast Fourier transform (FFT) layer to convert the PPG signal to PPG frequency representations, the FFT layer positioned after the first series of convolutional layers, and
(iii) a dense layer to decode the PPG frequency representations to respiratory rate predictions, the dense layer positioned after the FFT layer;
receiving a respiratory rate prediction output by the artificial neural network model, wherein the respiratory rate prediction represents the respiratory rate contained in the PPG data; and
storing the respiratory rate prediction in a storage medium to make the respiratory rate prediction available in response to a request.

14. The computer implemented method as recited in claim 13, further comprising preprocessing the PPG data received from the device prior to inputting the PPG data to the artificial neural network.

15. The computer implemented method as recited in claim 13, further comprising comparing a previous respiratory rate prediction to a current respiratory rate prediction to determine whether the current respiratory rate prediction is within a quality threshold of the previous respiratory rate prediction.

16. The computer implemented method as recited in claim 13, further comprising sending the respiratory rate prediction over a network to another device in response to a request for the respiratory rate prediction.

17. The computer implemented method as recited in claim 13, further comprising displaying the respiratory rate prediction on a display included in the device.

18. A non-transitory machine readable storage medium including instructions embodied thereon, wherein the instructions, when executed by at least one processor:
obtain a photoplethysmogram (PPG) dataset for training an artificial neural network model to predict a respiratory rate;
preprocess the PPG dataset to form a training PPG dataset;
train the artificial neural network model using the training PPG dataset, wherein the artificial neural network model includes:
a first series of convolutional layers to identify a PPG signal in PPG data and remove artifacts contained in the PPG data,
a fast Fourier transform (FFT) layer to convert the PPG signal to PPG frequency representations, the FFT layer positioned after the first series of convolutional layers, and
a dense layer to decode the PPG frequency representations to respiratory rate predictions, the dense layer positioned after the FFT layer; and
deploy the artificial neural network model to a production environment to predict respiratory rates.

19. The non-transitory machine readable storage medium as recited in claim 18, further comprising instructions, that when executed by the at least one processor:
calculate a Fourier transform of a prior respiratory rate prediction;
concatenate the Fourier transform of the prior respiratory rate prediction to a Fourier transform output by the FFT layer of the artificial neural network model to form a concatenated Fourier transform; and
provide the concatenated Fourier transform to the dense layer of the artificial neural network model.

20. The non-transitory machine readable storage medium as recited in claim 18, wherein the instructions, that when executed by at least one processor, train the artificial neural network model, further train the artificial neural network model using (i) categorical cross entropy to label the PPG dataset as a respiratory rate category and (ii) an Adam optimizer to update weights assigned to the PPG data.

* * * * *